United States Patent
Coats

(10) Patent No.: US 11,472,131 B2
(45) Date of Patent: Oct. 18, 2022

(54) INJECTION NOZZLE AND METHOD OF MAKING SAME

(71) Applicant: PORTAL INSTRUMENTS, INC., Cambridge, MA (US)

(72) Inventor: Andrew Owen Coats, Somerville, MA (US)

(73) Assignee: PORTAL INSTRUMENTS, INC., Cambridge, MA (US)

(*) Notice: Subject to any disclaimer, the term of this patent is extended or adjusted under 35 U.S.C. 154(b) by 475 days.

(21) Appl. No.: 16/527,837

(22) Filed: Jul. 31, 2019

(65) Prior Publication Data

US 2020/0039155 A1 Feb. 6, 2020

Related U.S. Application Data

(60) Provisional application No. 62/714,936, filed on Aug. 6, 2018.

(51) Int. Cl.
  *B29C 69/00* (2006.01)
  *A61M 5/30* (2006.01)

(52) U.S. Cl.
  CPC ......... *B29C 69/001* (2013.01); *A61M 5/3007* (2013.01); *A61M 2207/00* (2013.01); *B29C 2793/009* (2013.01)

(58) Field of Classification Search
  CPC ..... B29C 69/001; B29C 45/0053; A61M 5/30
  See application file for complete search history.

(56) References Cited

U.S. PATENT DOCUMENTS

| | | | |
|---|---|---|---|
| 2006/0116631 A1* | 6/2006 | Fukushima | A61M 5/30 604/68 |
| 2007/0055214 A1* | 3/2007 | Gilbert | A61M 5/30 604/500 |
| 2015/0129688 A1* | 5/2015 | Buchanan | B23K 26/388 239/589 |
| 2015/0374921 A1* | 12/2015 | Kojic | B05B 1/02 239/1 |
| 2016/0199579 A1* | 7/2016 | Boyd | A61M 5/30 604/70 |
| 2019/0016027 A1* | 1/2019 | Dehling | A61M 5/30 |

* cited by examiner

*Primary Examiner* — Kelly M Gambetta
*Assistant Examiner* — Virak Nguon
(74) *Attorney, Agent, or Firm* — Lando & Anastasi, LLP

(57) ABSTRACT

A material for an injection nozzle is molded into a form that includes a sacrificial tip around the nozzle exit orifice. The sacrificial tip is then machined away using any suitable machining process to expose the exit orifice. In this manner, an injection nozzle can be fabricated with favorable geometric characteristics.

21 Claims, 11 Drawing Sheets

INJECTION NOZZLE AND METHOD OF MAKING SAME

CROSS REFERENCE TOP RELATED APPLICATIONS

This application claims priority under 35 U.S.C. § 119(e) to U.S. Provisional Patent Application Ser. No. 62/714,936, titled "INJECTION NOZZLE AND METHOD OF MAKING SAME," filed Aug. 6, 2018, which is incorporated by reference herein in its entirety for all purposes.

TECHNICAL FIELD

This disclosure relates to high velocity needle-free transdermal injection devices and to methods of forming nozzles for same.

BACKGROUND

In medicine, injectates such as drugs may be delivered through the skin of a patient and into the bloodstream. Traditionally, this delivery of liquids into a patient's body is accomplished by insertion of a needle through the patient's skin and into an area where the liquid can enter the patient's blood stream. However, needles have a number of significant drawbacks such as the pain associated with being pierced by a needle, the fear that many patients have of needles, skin damage and associated risks of infection, and the need for proper disposal of needles after injection. While useful needle-free injectors have been developed as an alternative, such as those described in U.S. Pat. Pub. No. 2017/0143906, which is incorporated herein by reference in its entirety, there remains a need for improved techniques for fabricating injection nozzles for use with these needle-free devices.

SUMMARY

In accordance with an aspect of the present disclosure, a material for an injection nozzle is molded into a form that includes a sacrificial tip around the nozzle exit orifice. The sacrificial tip is then machined away using any suitable machining process to expose the exit orifice. In this manner, an injection nozzle can be fabricated with favorable geometric characteristics.

In accordance with another aspect, there is provided a method for fabricating an injection nozzle. The method comprises forming a nozzle including an interior nozzle geometry having an axis between an opening at a first end of the interior nozzle geometry and an orifice at a second end of the interior nozzle geometry, the orifice having a smaller cross section than the opening, the nozzle further including a sacrificial tip extending beyond and occluding the orifice, and machining the nozzle with a subtractive process to remove the sacrificial tip and expose the orifice.

In some embodiments, forming the nozzle comprises one or more of injection molding the nozzle, stamping the nozzle, forming the nozzle by a process comprising embossing the nozzle, 3D printing the nozzle, casting the nozzle, or thermoforming the nozzle. Machining the nozzle may comprise one or more of laser machining the nozzle, milling the nozzle, drilling the nozzle, or electrical discharge machining the nozzle.

In some embodiments, forming the nozzle comprises forming the nozzle with the interior nozzle geometry including a substantially exponential taper from the opening to the orifice.

In some embodiments, forming the nozzle comprises forming the nozzle with the orifice having a diameter of less than three hundred micrometers.

In some embodiments, forming the nozzle comprises forming the nozzle with a path from the opening to the orifice being less than 1.75 millimeters.

In some embodiments, forming the nozzle comprises forming the nozzle with a wall of the interior nozzle geometry asymptotically approaching a slope of the axis at the orifice.

In some embodiments, forming the nozzle comprises forming the nozzle with a wall of the interior nozzle geometry approaching a slope of the axis at a rate of between $e^{-0.0031372x}$ and $e^{-0.003463x}$, where x is a distance in millimeters along the axis from the opening toward the orifice.

In some embodiments, the method further comprises positioning a fluid chamber adjacent to and in fluid communication with the opening.

In some embodiments, the method further comprises coupling a fluid chamber to the nozzle by disposing the nozzle within a cartridge defining the fluid chamber and adhering an outer surface of the nozzle to an inner wall of the cartridge. Adhering the outer surface of the nozzle to the inner wall of the cartridge may comprise one of adhering the outer surface of the nozzle to the inner wall of the cartridge with an adhesive or adhering the outer surface of the nozzle to the inner wall of the cartridge by welding. Adhering the outer surface of the nozzle to the inner wall of the cartridge may comprise adhering the outer surface of the nozzle to the inner wall of the cartridge by laser welding. Adhering the outer surface of the nozzle to the inner wall of the cartridge may comprise adhering the outer surface of the nozzle to the inner wall of the cartridge in a position in which a lower periphery of the nozzle engages an internal shoulder portion of the cartridge. Adhering the outer surface of the nozzle to the inner wall of the cartridge may comprise adhering the outer surface of the nozzle to the inner wall of the cartridge in a position in which a lower periphery of the nozzle engages an outlet conduit of the cartridge on the opposite side of the nozzle from the fluid chamber.

In some embodiments, forming the nozzle comprises forming the nozzle from one of a polymer, a metal, or a glass. Forming the nozzle may comprise forming the nozzle from one or more of a cyclic olefin polymer, a cyclic olefin copolymer, polycarbonate, polypropylene, glass, or silicon borate.

In some embodiments, the method further comprises locating the interior nozzle geometry within the nozzle and machining the sacrificial tip to a predetermined distance from the opening along the axis.

In some embodiments, the method further comprises machining the sacrificial tip to remove material along the axis until the orifice reaches a predetermined size.

In some embodiments, the method further comprises machining the sacrificial tip to remove material along the axis until a wall of the interior nozzle geometry at the orifice is substantially parallel to the axis.

In some embodiments, the method further comprises machining a surface about the orifice substantially normal to the axis of the nozzle.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

A needle-free transdermal injection device may effectively deliver an injectate through the skin of a subject when the injectate is expelled from the injection device at a high velocity in a narrow, collimated stream. A narrow, collimated stream of injectate may disperse the injectate over a small area of the skin of the subject, reducing the amount of discomfort or pain the subject may experience during injection of the injectate and may deliver the injectate with a high pressure per unit area, making it easier for the injectate to penetrate the skin. As disclosed in US Patent Publication No. 2018/0078704, which is incorporated herein by reference in its entirety for all purposes, the configuration of the nozzle of a needle-free transdermal injection device may have a significant impact on characteristics of the injection such as the dispersion, the velocity, and the turbulence or shear in an injectate when passing through the nozzle. Turbulence or shear may be of particular concern when delivering therapeutics that might be damaged by the high accompanying forces.

In some embodiments, nozzles for needle-free transdermal injection devices include generally continuous, smooth internal surfaces with well-defined geometries and exit orifices having diameters of 300 μm or less, for example, as small as about 50 μm. Suitable geometries may be formed by injection molding. Conventional injection molding techniques, however, may produce an undesirably high amount of nozzles having one or more forms of defects, particularly around fine features such as the nozzle exit where draft angles and draw paths for the mold may constrain geometry or impose molding artifacts.

While the following description focuses on fabrication of injection nozzles for needle-free delivery of injectates, it will be appreciated that the principles disclosed herein may be usefully applied to the fabrication of any other nozzle or other fluid delivery device with similar geometric constraints, material constraints, and/or functional constraints. For example, the techniques disclosed herein may usefully be applied to fabricate water jet nozzles for waterjet cutting machines, or any other nozzles, jets or the like benefiting from more collimated, high-pressure fluid streams.

Figure 1:
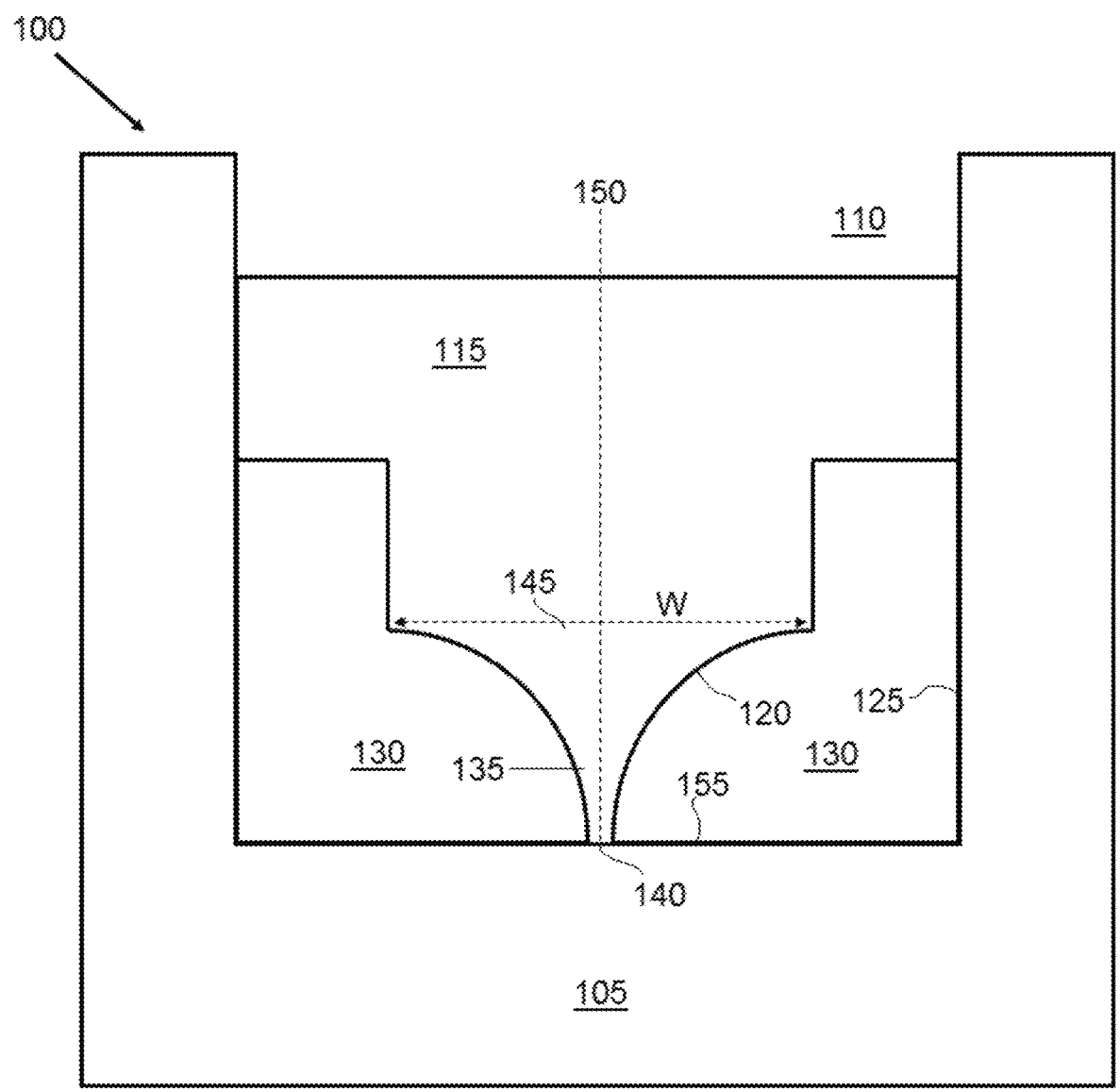
FIG. 1 illustrates a mold for injection molding a nozzle for a needle-free transdermal injection device.

FIG. 1 illustrates a cross-section of a mold for injection molding a nozzle for a needle-free transdermal injection device. The mold 100 may include a first mold element 105 that defines a hollow space 110 in which the nozzle is formed, and a second mold element 115 that fits into the hollow space 110 defined in the first mold element 105. The second mold element 115 may include an external surface 120, which in combination with an internal surface 125 of the first mold element 105, defines a cavity 130 having the shape of the nozzle to be formed. A lower portion of the second mold element 115, referred to as the pin section 135 of the second mold element 115, decreases in cross-sectional area until it terminates at a lower end 140 that defines the exit orifice of the nozzle. As discussed above, the exit orifice of the nozzle may, in some embodiments, have a diameter of about 50 μm. The lower end 140 of the pin section 135 of the second mold element 115 may thus also have a diameter of about 50 μm.

An upper end 145 of the pin section 135 defines the opening of the nozzle and may have a width W of about 3 mm. The nozzle may have an axis 150 that extends perpendicular to the upper internal surface 155 of the first mold element 105 and that is centered within the second mold element 115. The first mold element 105 and the second mold element 115 may be rotationally symmetrical about the axis 150. A distance between the opening of the nozzle and the exit orifice of the nozzle may be less than 1.75 mm, for example, about 1.5 mm. The external surface 120 of the second mold element 115 may exhibit a substantially exponential taper from the upper end 145 of the pin section 135 defining the opening of the nozzle to the lower end 140 of the pin section 135 defining the orifice of the nozzle. The external surface 120 of the second mold element 115 may exhibit a geometry asymptotically approaching a slope of the axis 150 at the lower end 140 of the pin section 135 defining the orifice of the nozzle. The external surface 120 of the second mold element 115 may exhibit a geometry approaching a slope of the axis 150 at the lower end 140 of the pin section 135 at an exponential rate of between about $e^{-0.0031372x}$ and $e^{-0.003463x}$, where x is a distance in millimeters along the axis 150 from the upper end 145 of the pin section 135 defining the opening of the nozzle toward the lower end 140 of the pin section 135 defining the orifice of the nozzle. A nozzle formed in the mold 100 may have an internal surface with a geometry matching the geometry of the external surface 120 of the second mold element 115.

Figure 2A:
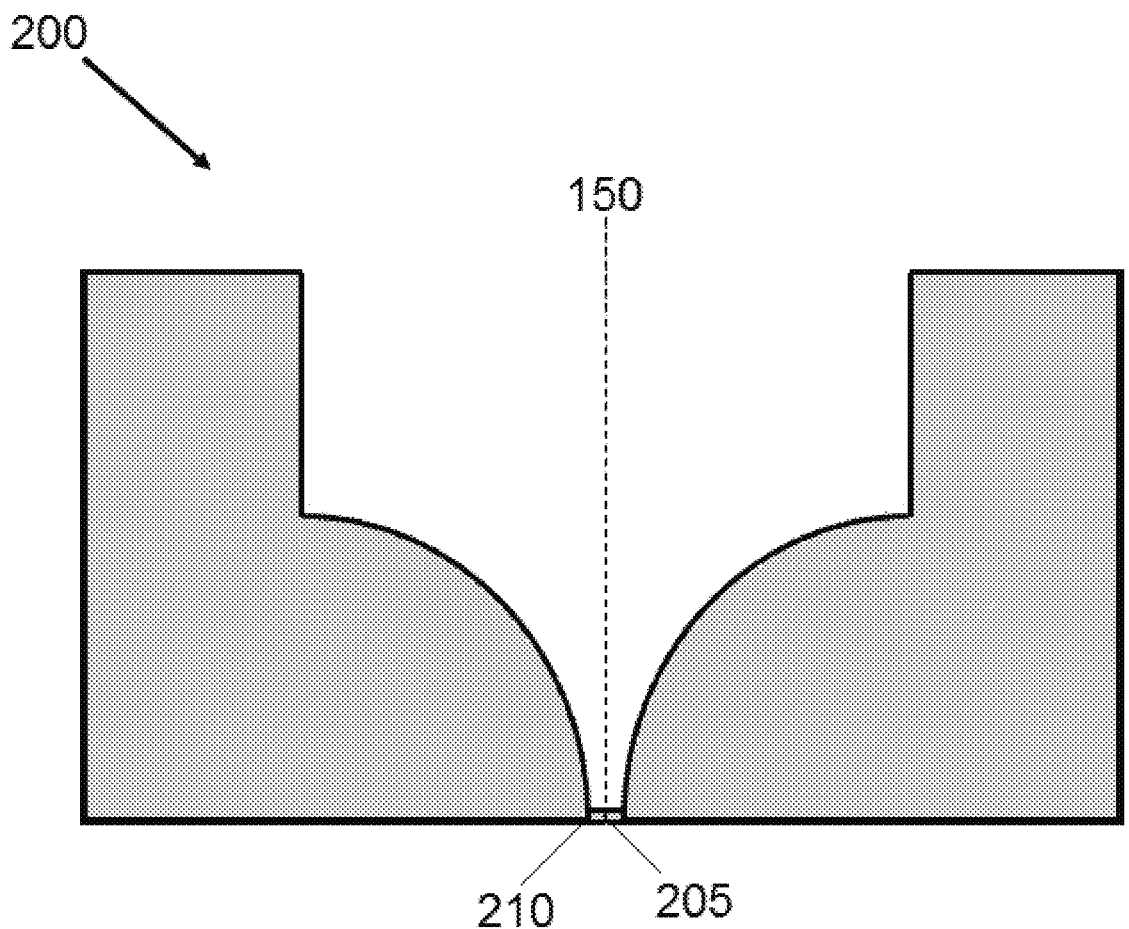
FIG. 2A illustrates a first type of defect that may be present in a nozzle.

While injection molding generally supports small feature sizes, it can be challenging to form certain geometries such as narrow channels or openings. During the injection molding process, a material from which the nozzle is formed, for example, a polymer including or consisting of one or more of a cyclic olefin polymer, a cyclic olefin copolymer, polycarbonate, polypropylene, or another suitable polymer or glass is injected under pressure into the cavity 130 defined in the mold 100. In some instances, even where the mold retains its shape throughout injection, after the injection molded nozzle 200 is removed from the mold a piece of material 205, referred to as "flash" may remain and partially or fully occlude the exit orifice 210 of the nozzle 200 as illustrated in FIG. 2A. The flash 205 may form, for example, where the lower end 140 of the pin section 135 of the of the second mold element 115 is not in proper contact with the upper internal surface 155 of the first mold element 105, e.g., due to insufficient pressure applied between the first mold element 105 and second mold element 115, or due to excess pressure applied to the injected material during injection molding of the nozzle.

Figure 2B:
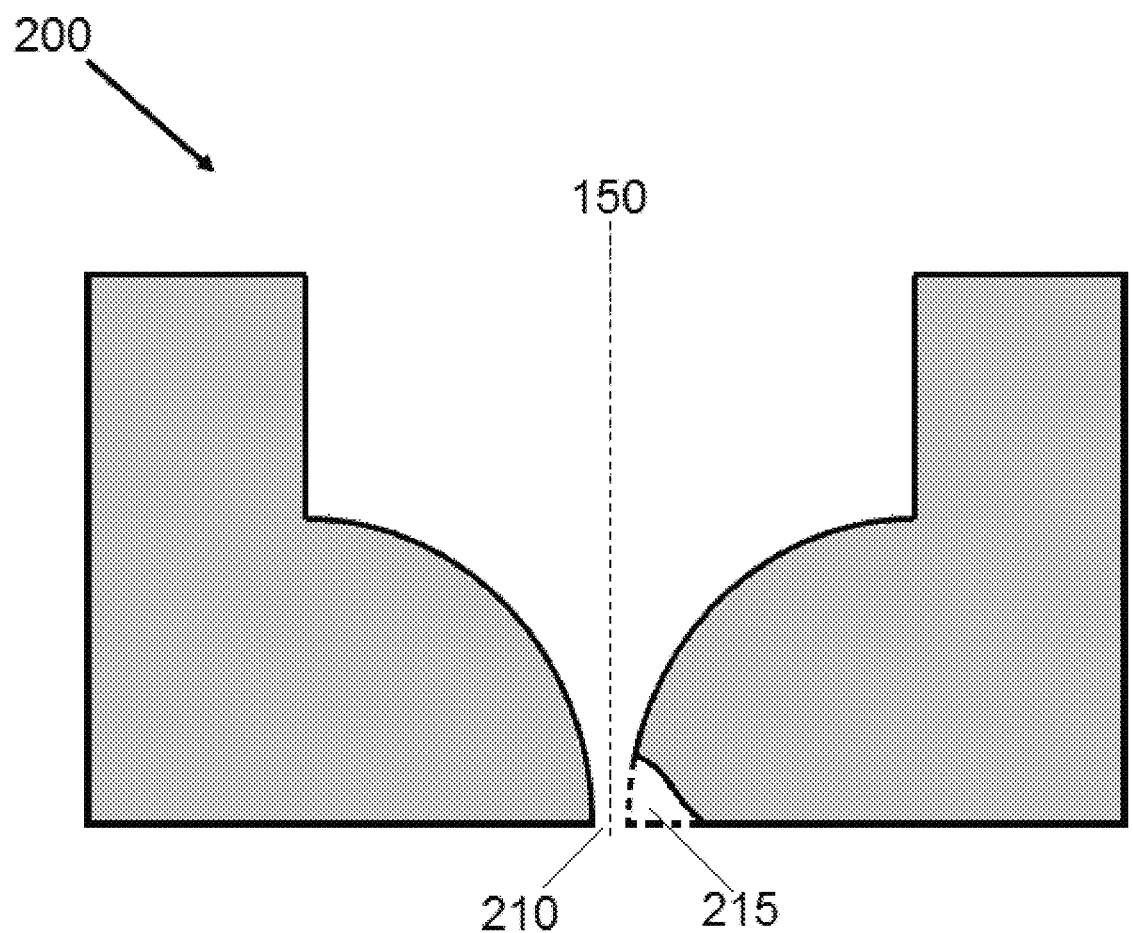
FIG. 2B illustrates a second type of defect that may be present in a nozzle.

Another form of defect that may occur during injection molding of the nozzle 200 is the formation of a void 215, illustrated in FIG. 2B, where injection molding material did not fully fill the cavity 130 defined between the first mold element 105 and second mold element 115. Voids 215 may form from, for example, insufficient pressure applied to the injected material during injection molding of the nozzle or an air bubble being present in the injection molding material.

The presence of the flash 205 and/or a void 215 adjacent the exit orifice 210 of the nozzle 200 may interfere with nozzle geometry and decrease the performance of the nozzle when used in a needle-free transdermal injection device, or may render the nozzle non-functional for use in a needle-free transdermal injection device by, for example, blocking the flow of injectate from the device or altering a flow pattern of injectate from the device.

Figure 3:
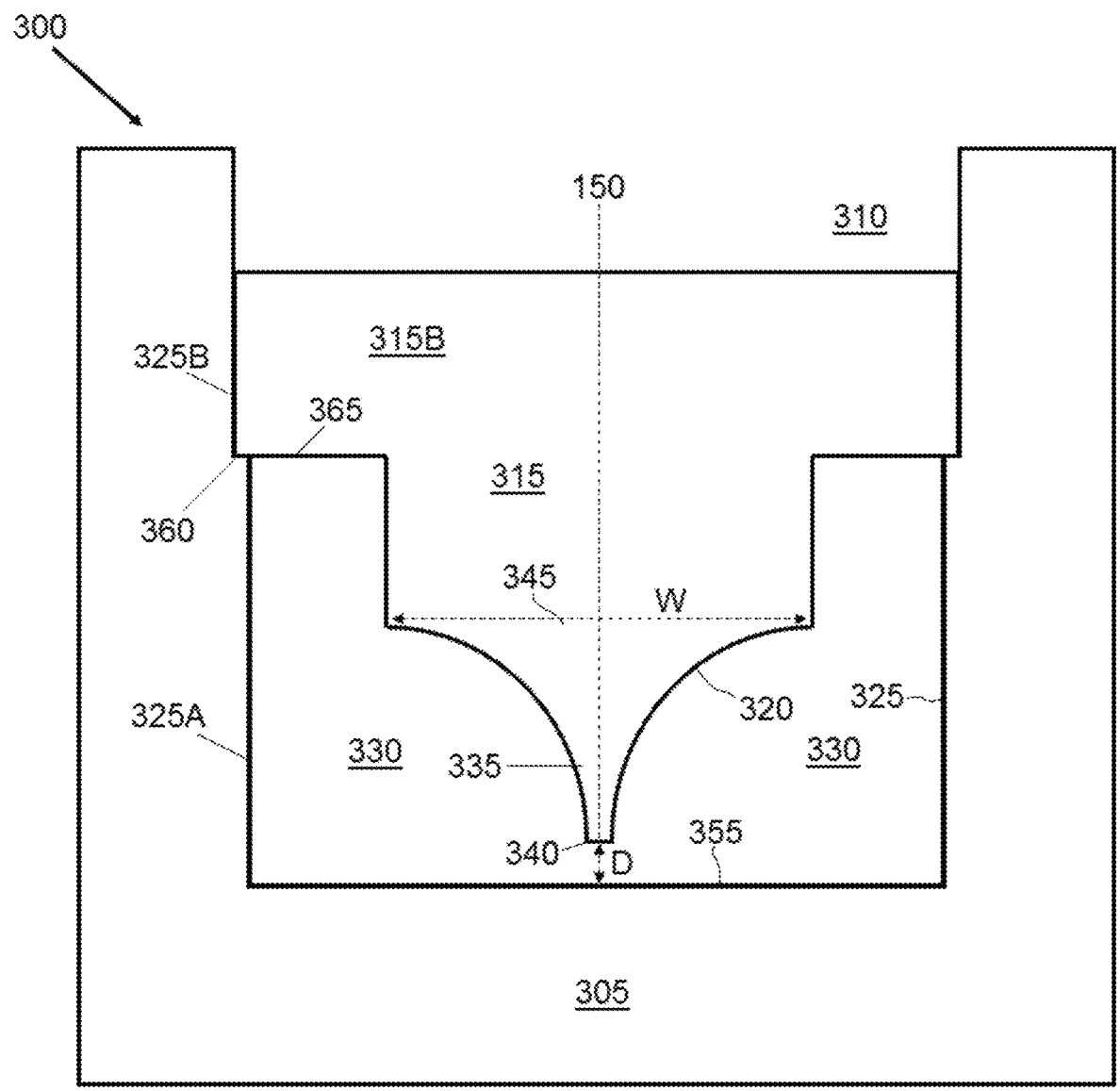
FIG. 3 illustrates another mold for injection molding a nozzle for a needle-free transdermal injection device.

An alternate methodology of forming a nozzle utilizing a mold 300 may reduce or eliminate the probability of the occurrence of defects such as flash or voids in injection molded nozzles. One embodiment of an alternate mold 300 is illustrated in FIG. 3 in which features corresponding to those of mold 100 are indicated with similar reference numbers but beginning with a 3 instead of a 1. Mold 300 is similar to mold 100 except the second mold element 315 (corresponding to second mold element 115 of mold 100) does not contact the upper internal surface 355 of the first mold element 305 (corresponding to first mold element 105 of mold 100). Rather, when the first mold element 305 is fully inserted into the hollow space 310 defined in the first mold element 305, the lower end 340 of the pin section 335 of the second mold element 315 is spaced a distance D from the upper internal surface 355 of the first mold element 305. Distance D may be, for example, between 100 µm and 5 mm, between 0.5 mm and 1 mm, between 1 mm and 3 mm, or any other distance providing a suitable geometry for carrying a flow of needle-free injectate. In some embodiments, distance D is defined by a lower portion 325A of the internal surface 325 of the first mold element 305 that extends further into the hollow space 310 than an upper portion 325B of the internal surface 325 of the first mold element 305 and defines a stop or shoulder 360. When the second mold element 315 is inserted into the hollow space 310 defined in the first mold element 305, a lower surface 365 of an upper portion 315B of the second mold element 315 comes into contact with the stop or shoulder 360 which prevents the second mold element 315 from being further inserted into the hollow space 310.

Figure 4:
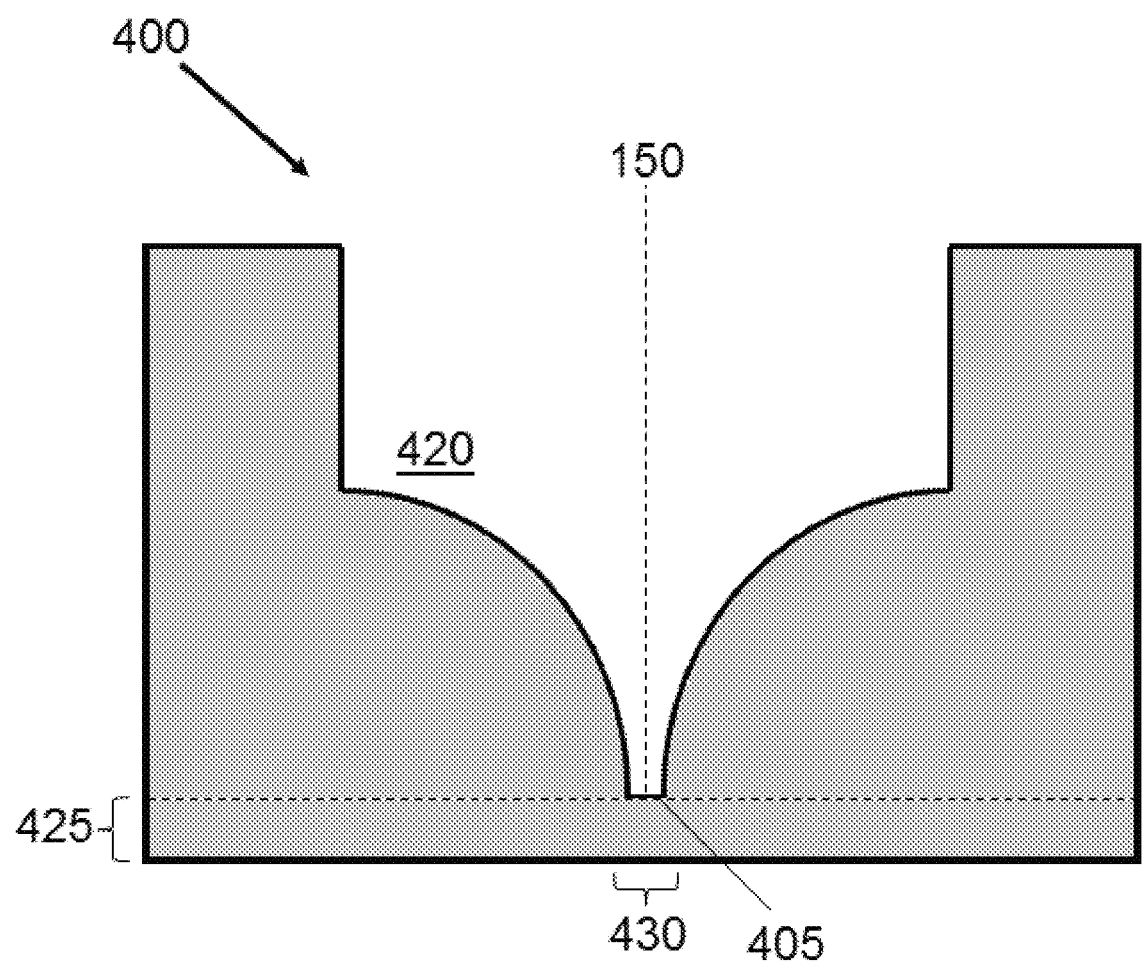
FIG. 4 illustrates a formed nozzle.

When a nozzle 400, illustrated in FIG. 4, is removed from the mold 300 after injection molding the nozzle 400 has an interior nozzle geometry 420 with an orifice 405 that is occluded by a material layer 425 including a sacrificial tip portion 430.

Nozzle 400 has been described above as being formed by injection molding, however, in alternate embodiments, different manufacturing techniques may be used to form nozzle 400. Nozzle 400 may alternatively be formed by any of, for example, stamping, molding, embossing, 3D printing, casting, or thermoforming. A particular manufacturing technique may be selected based on, for example, a desired shape of the nozzle and/or a desired material of which the nozzle may be formed. The nozzle 400 may formed of any one or more of a polymer, a metal, or a glass. The nozzle 400 may formed of any one or more of, for example, cyclic olefin copolymer, cyclic olefin polymer, polycarbonate, polypropylene, glass (e.g., $SiO_2$, borosilicate glass, soda-lime-silica glass, etc.), and so forth. The material of the nozzle 400 may be selected based on a type of medicament or injectate to be delivered through the nozzle 400. For example, for injection devices intended to dispense injectates that may react with or degrade when in contact with polycarbonate or polypropylene the nozzle 400 may desirably be formed of cyclic olefin copolymer, cyclic olefin polymer, or glass.

Figure 5A:
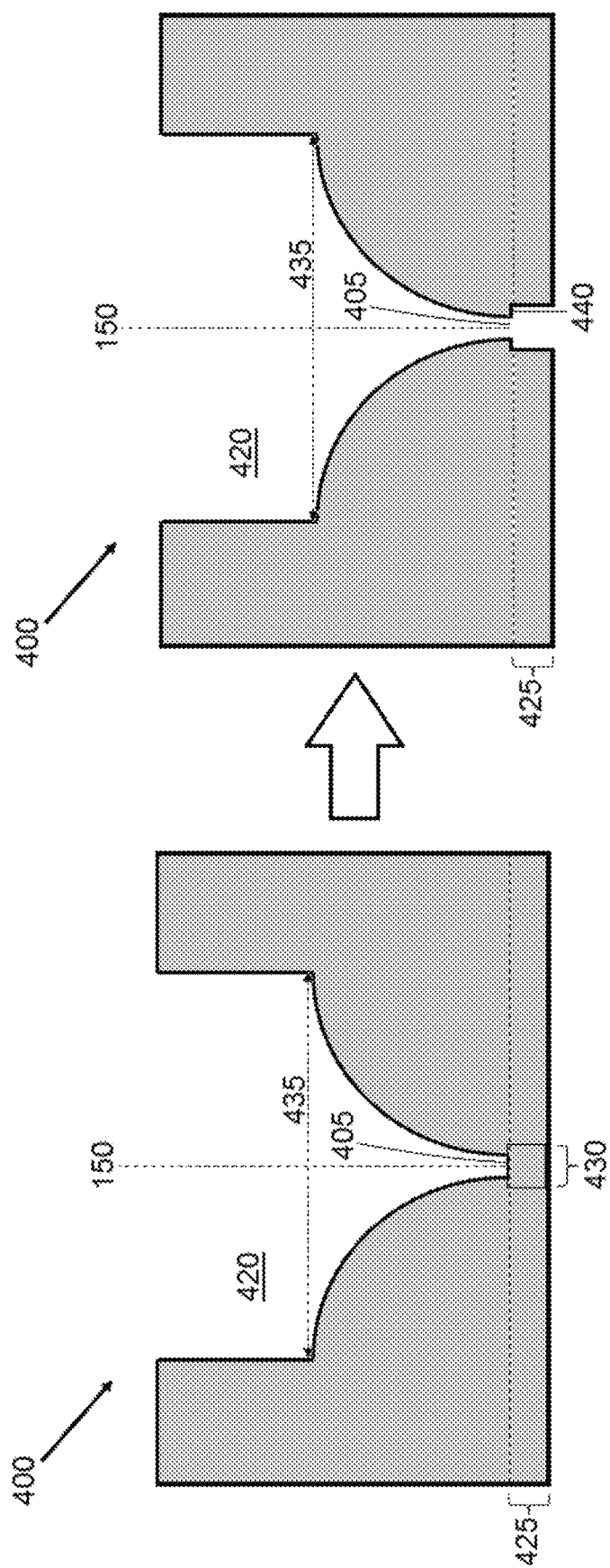
FIG. 5A illustrates a first method of opening the orifice of the nozzle of FIG. 4.
Figure 5B:
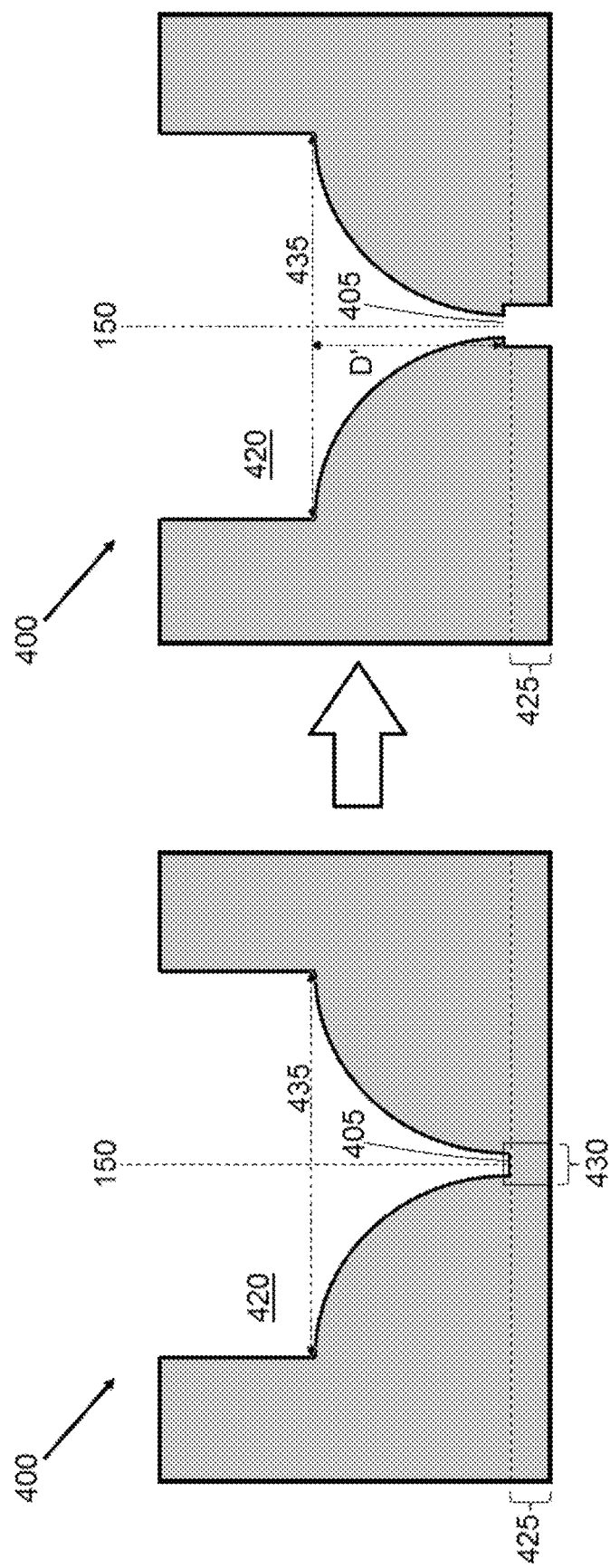
FIG. 5B illustrates a second method of opening the orifice of the nozzle of FIG. 4.

After the material for the nozzle 400 is shaped as described above, further processing may be performed to open up the orifice 405, for example, by removing at least a portion of the sacrificial tip portion 430 or other portions of the material layer 425 at or around the orifice 405. In some embodiments, as illustrated in FIG. 5A, the sacrificial tip portion 430 is removed to open up the orifice 405, while the remainder of the material layer 425 is left in place. The sacrificial tip portion 430 that is removed may have a height just sufficient to expose the orifice 405, as illustrated in FIG. 5A. Alternatively, as illustrated in FIG. 5B, a height of the sacrificial tip portion 430 that is removed may be greater than the height of the material layer 425. The height of the material that is removed may extend above the lower extent of the portion of the nozzle formed by the lower end 140 of the pin section 135 of the of the second mold element 115 in embodiments in which the nozzle is formed by injection molding. The width of the sacrificial tip portion 430 that is removed may be greater than the width of the orifice 405, and may usefully include any width up to and including the entire width of the nozzle 400 in a plane perpendicular to the axis 150, or substantially perpendicular to the axis 150 (or otherwise oriented to the axis in a manner that achieves a desired injectate stream). The width of the sacrificial tip portion 430 that is removed may be, for example, between 1.5 and 10 times or between 3 and 8 times the width of the orifice 405. More generally, any amount of material consistent with proper operation of the nozzle 400 and consistent with available machining tools or the like, may usefully be removed as contemplated herein. When the sacrificial tip portion 430 that is removed has a width greater than the width of the orifice 405, this may relax tool tolerances by helping to ensure smoothly converging sidewalls around the exit region. This may also provide significant advantages over other machining techniques such as drilling the orifice, which might otherwise present greater physical challenges such as aligning tool material removal precisely with interior nozzle walls in a manner that maintains a smooth, continuous exit profile.

Removing the sacrificial tip portion 430 may include machining the sacrificial tip portion 430 a predetermined distance (distance D' in FIG. 5B) from the opening 435 of the nozzle 400 along the axis 150, or a predetermined distance relative to any other feature of, or location on, the nozzle 400. Removing the sacrificial tip portion 430 may include machining the sacrificial tip portion 430 to remove material along the axis 150 until the orifice 405 reaches a predetermined size, for example, a predetermined diameter or cross-sectional area. Removing the sacrificial tip portion 430 may also or instead include machining the sacrificial tip portion 430 to remove material along the axis 150 until a wall of the interior nozzle geometry at the orifice 405 is substantially parallel to the axis 150. Removing the sacrificial tip portion 430 may include machining a surface about the orifice 405, for example, the surface 440 in FIG. 5A, substantially normal to the axis 150 of the nozzle 400.

The mechanism used to remove the sacrificial tip portion 430 from the nozzle 400 may be selected, for example, based on the material from which the nozzle is formed 400 and is not particularly limited to any one specific mechanism. Machining of the sacrificial tip portion 430 from the nozzle 400 may include any of, for example, laser machining, milling, drilling, electrical discharge machining, or other forms of machining known in the art.

Figure 6A:
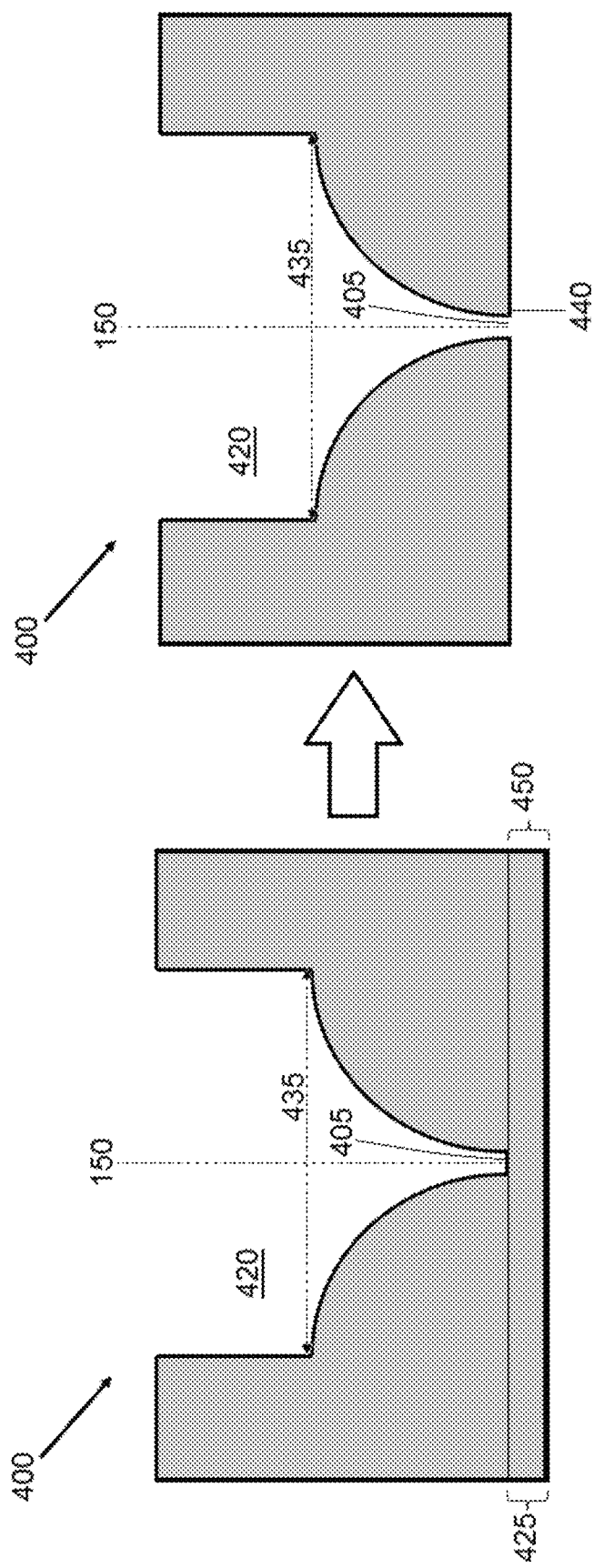
FIG. 6A illustrates a third method of opening the orifice of the nozzle of FIG. 4.
Figure 6B:
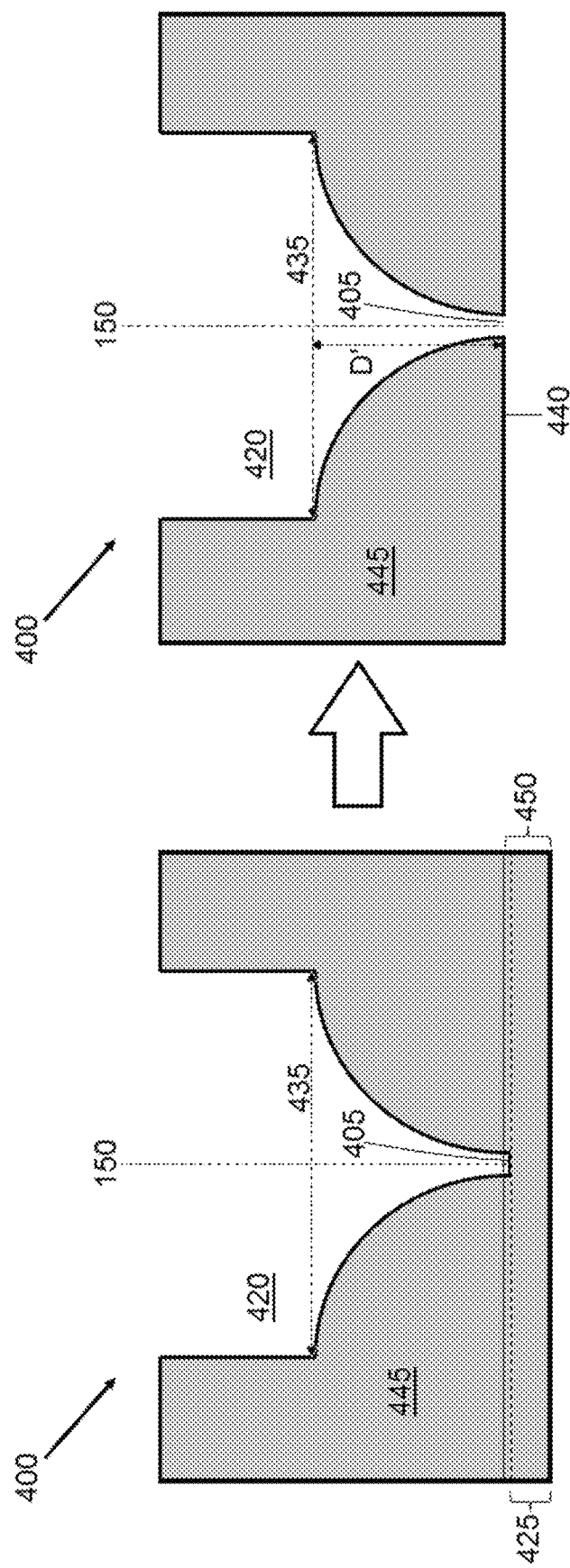
FIG. 6B illustrates a fourth method of opening the orifice of the nozzle of FIG. 4.

In other embodiments, instead of removing only the sacrificial tip portion 430 to open the orifice 405 of the nozzle 400, the entire material layer 425 and, optionally, additional material is removed from the bottom of the nozzle 400 to open the orifice 405. FIG. 6A illustrates an embodiment in which the material layer 450 that is removed has a height that is coextensive with that of material layer 425 and is just sufficient to expose the orifice 405. Alternatively, as illustrated in FIG. 6B, the material layer 425 and an additional amount of the body 445 of the nozzle 400 together form a layer 450 having a height greater than that of material layer 425. Material layer 450 is removed to open the orifice 405. Removal of the additional amount of the body 445 of the nozzle 400 may bring the opening of the orifice 405 above the lower extent of the portion of the nozzle formed by the lower end 140 of the pin section 135 of the of the second mold element 115 in embodiments in which the nozzle was formed by injection molding.

Removing the material layer 450 may include machining the material layer 450 using predetermined geometric constraints, such as by removing material until a lower surface of the nozzle 400 (for example, surface 440) is a predetermined distance (distance D' in FIG. 6B) from the opening 435 of the nozzle 400 along the axis 150. Removing the material layer 450 may also or instead include geometric or other feedback. For example, removing the material layer 450 may include machining the bottom of the nozzle to remove material along the axis 150 until the orifice 405 reaches a predetermined size, for example, a predetermined diameter, or removing the material layer 450 may include machining the material layer 450 to remove material along the axis 150 until a wall of the interior nozzle geometry at the orifice 405 is substantially parallel to the axis 150. Thus, one or more physical characteristics of the nozzle 400 may be measured during machining in order to provide suitable feedback to control the machining process. Removing the material layer 450 may include machining a surface about the orifice 405, for example, surface 440, substantially normal to the axis 150 of the nozzle 400, which may be the same machining process that removes the material layer 450 as described above, or a supplemental machining process to level the surface after other machining is complete.

The mechanism used to remove the material layer 450 from the nozzle 400 may be selected, for example, based on the material from which the nozzle is formed 400 and is not particularly limited to any one specific mechanism. Machining of the material layer 450 from the nozzle 400 may include any of, for example, laser machining, milling, drilling, electrical discharge machining, or other forms of machining known in the art.

It is to be understood that the particular shape of the nozzle 400 illustrated is not limiting. For example, in some embodiments, the portion of the nozzle 400 above the opening 435 may include an internal and/or external outward taper as illustrated in US Patent Publication No. 2018/0078704.

After processing to open the orifice 405 of the nozzle 400, the nozzle 400 may be integrated into or otherwise coupled to a fluid chamber which may include or be configured to include injectate for delivery through the skin of a subject using a needle-free transdermal injection device. The fluid chamber may be coupled to the opening 435 of the nozzle 400 so the injectate may be delivered into the opening 435 and through the orifice 405 of the nozzle 400. In some embodiments, the nozzle 400 is disposed and affixed within a cartridge defining the fluid chamber. In other embodiments, coupling the fluid chamber to the opening 435 of the nozzle 400 comprises forming the fluid chamber adjacent to and coupled in fluid communication with the opening 435 of the nozzle 400.

Figure 7:
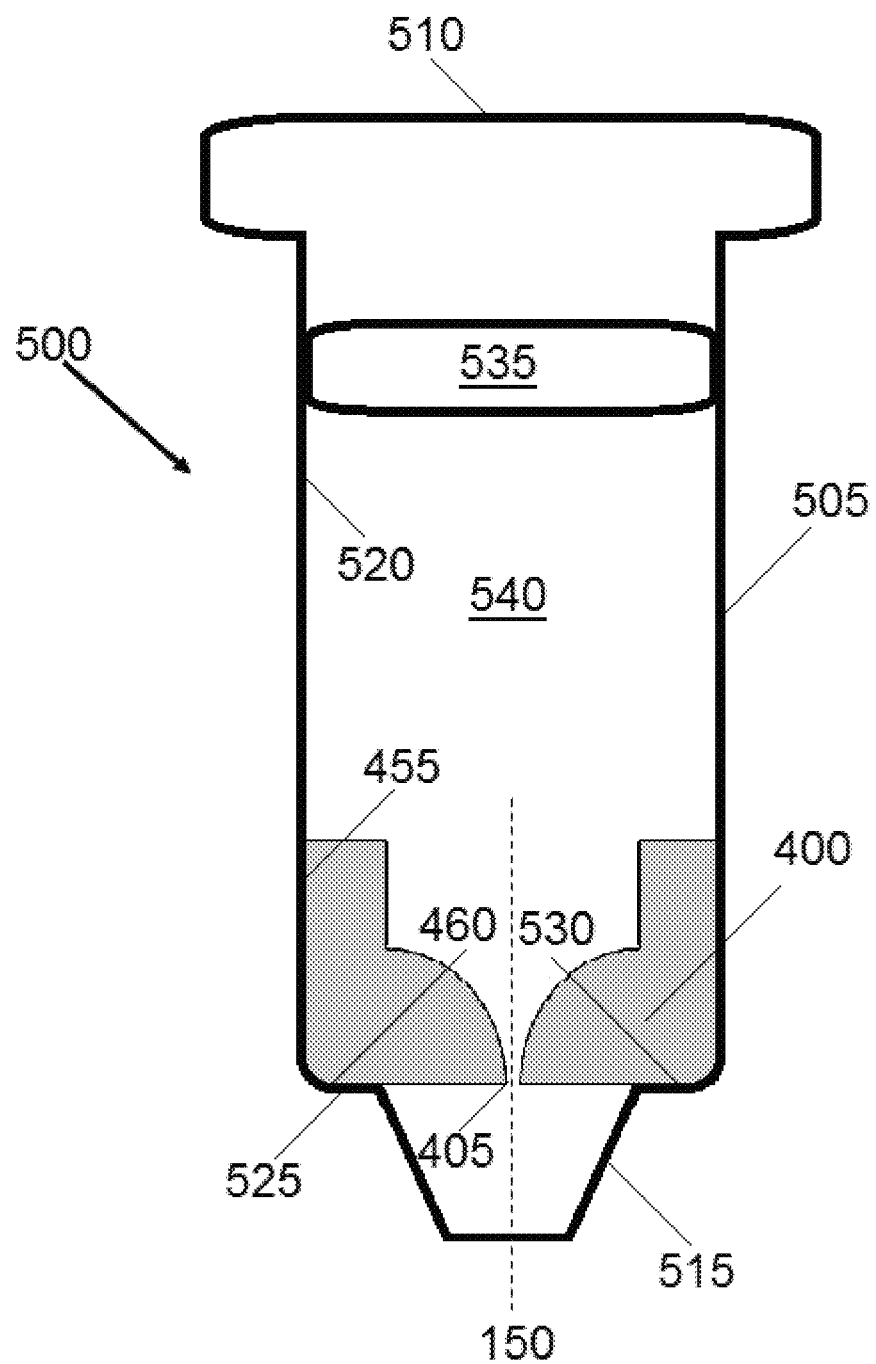
FIG. 7 illustrates a nozzle disposed in a cartridge.

An embodiment of an injectate cartridge 500 for a needle-free transdermal injection device is illustrated in FIG. 7. The cartridge 500 may include a wall 505, for example, a cylindrical or substantially cylindrical wall 505, an inlet port 510, and an outlet port or conduit 515. The material(s) of the cartridge 500 are not particularly limited, but may be any of the materials disclosed above of which the nozzle 400 is formed. An embodiment of a nozzle 400 is disposed within the cartridge 500. The nozzle 400 and the outlet port or conduit 515 may share a common axis 150 such that the orifice 405 of the nozzle 400 is substantially centered above the outlet port or conduit 515.

An outer circumferential wall or surface 455 of the nozzle 400 may be adhered to an inner surface 520 of the wall 505 of the cartridge 500. The nozzle 400 may be adhered to the inner surface 520 of the wall 505 of the cartridge 500 with an adhesive, for example, epoxy, cyanoacrylate, plastic cement, or any other adhesive compatible with the material(s) of the nozzle 400 and cartridge 500. In other embodiments, the nozzle 400 may be adhered to the inner surface 520 of the wall 505 of the cartridge 500 by welding, for example, by thermal welding or laser welding.

The wall 505 of the cartridge 500 may include a portion that transitions from sides of the cartridge 500 to the outlet port or conduit 515. The transitional portion of the wall 505 of the cartridge 500 may define a shoulder portion 525. The outer surface 455 of the nozzle 400 may be adhered to the inner surface 520 of the wall 505 of the cartridge 500 in a position in which a lower portion, for example, a lower periphery 460 of the nozzle 400 engages an internal wall 530 of the shoulder portion 525 of the cartridge 500.

A plunger 535 may be disposed within the body of the cartridge 500 and may define a fluid chamber 540 that is filled with or configured to be filled with an injectate. The outer surface 455 of the nozzle 400 may be adhered to the inner surface 520 of the wall 505 of the cartridge 500 in a position in which a lower portion, for example, the lower periphery 460 of the nozzle 400 engages the outlet conduit 515 of the cartridge 500 on the opposite side of the nozzle 400 from the fluid chamber 540.

Figure 8:
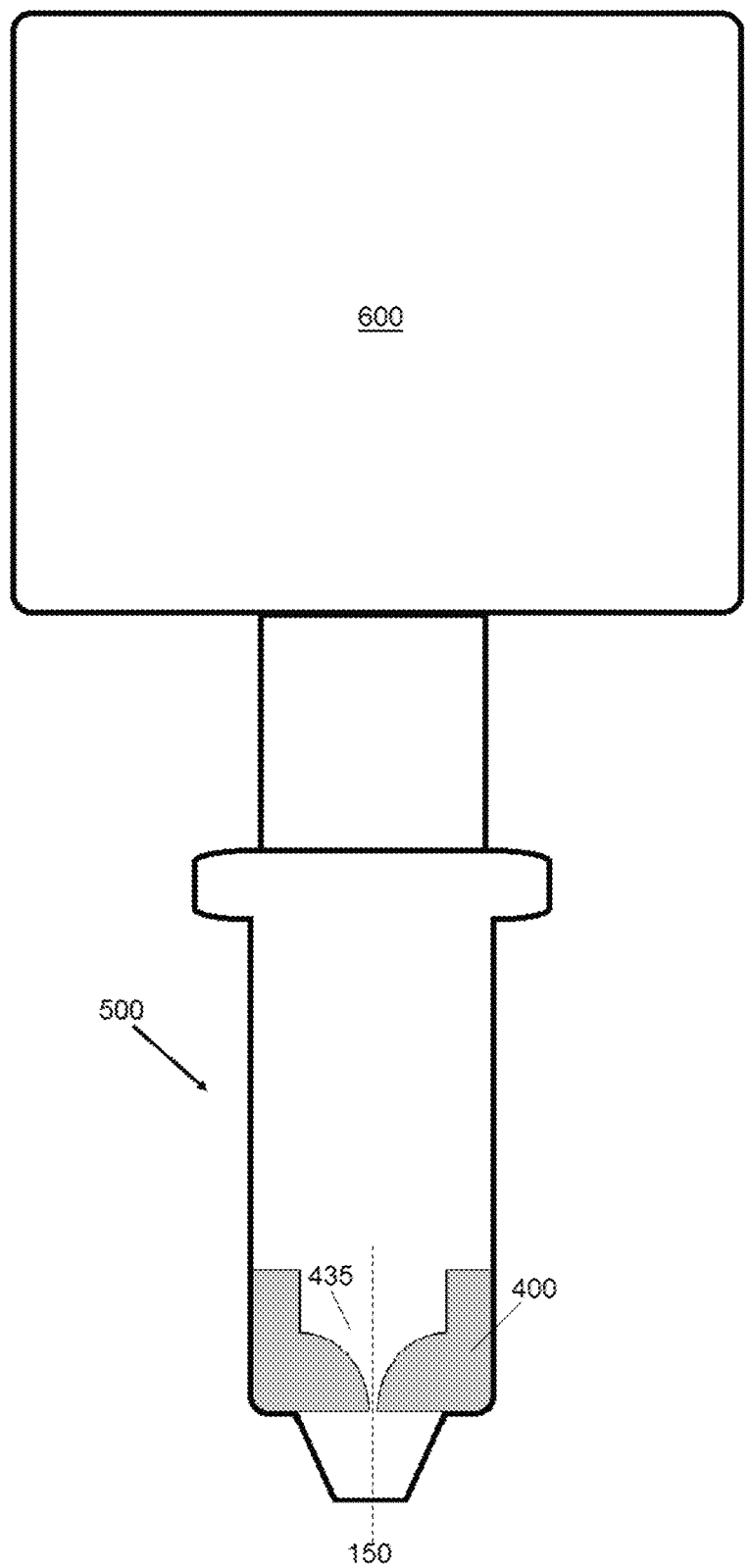
FIG. 8 illustrates a nozzle disposed in a cartridge connected to an external fluid chamber.

In another embodiment, illustrated in FIG. 8, the cartridge 500 may be fluidly coupled to an external fluid chamber 600. The external fluid chamber 600 may have a greater volume than the cartridge 500. The fluid chamber 600 may be coupled to the opening 435 of the nozzle 400 by forming the fluid chamber 600 adjacent to and coupled in fluid communication with the opening 435 of the nozzle 400, for example, via the cartridge 500.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. It is to be appreciated that embodiments of the methods and apparatuses discussed herein are not limited in application to the details of construction and the arrangement of components set forth in the foregoing description or illustrated in the accompanying drawings. The methods and apparatuses are capable of implementation in other embodiments and of being practiced or of being carried out in various ways. Examples of specific implementations are provided herein for illustrative purposes only and are not intended to be limiting. One or more features of any embodiment disclosed herein may be added to or substituted for any one or more features of any other embodiment. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation. Accordingly, the foregoing description and drawings are by way of example only.

What is claimed is:

1. A method for fabricating an injection nozzle, the method comprising:
    forming a nozzle including an interior nozzle geometry having an axis between an opening at a first end of the interior nozzle geometry and an orifice at a second end of the interior nozzle geometry, the orifice having a smallest cross-sectional area in a plane normal to the axis than any other portion of the interior nozzle geometry upon completion of formation of the nozzle, the nozzle further including a sacrificial tip extending beyond and occluding the orifice; and
    machining the nozzle with a subtractive process to remove the sacrificial tip and expose the orifice, the cross-sectional area of the orifice not being increased by the subtractive process.

2. The method of claim 1, wherein forming the nozzle comprises one or more of injection molding the nozzle, stamping the nozzle, forming the nozzle by a process comprising embossing the nozzle, 3D printing the nozzle, casting the nozzle, or thermoforming the nozzle.

3. The method of claim 2, wherein machining the nozzle comprises one or more of laser machining the nozzle, milling the nozzle, drilling the nozzle, or electrical discharge machining the nozzle.

4. The method of claim 1, wherein forming the nozzle comprises forming the nozzle with the interior nozzle geometry including an exponential taper from the opening to the orifice.

5. The method of claim 1, wherein forming the nozzle comprises forming the nozzle with the orifice having a diameter of less than three hundred micrometers.

6. The method of claim 1, wherein forming the nozzle comprises forming the nozzle with a path from the opening to the orifice being less than 1.75 millimeters.

7. The method of claim 1, wherein forming the nozzle comprises forming the nozzle with a wall of the interior nozzle geometry asymptotically approaching a slope of the axis at the orifice.

8. The method of claim 1, wherein forming the nozzle comprises forming the nozzle with a wall of the interior nozzle geometry approaching a slope of the axis at a rate of between $e^{-0.003172x}$ and $e^{-0.003463x}$, where x is a distance in millimeters along the axis from the opening toward the orifice.

9. The method of claim 1, further comprising positioning a fluid chamber adjacent to and in fluid communication with the opening.

10. The method of claim 1, further comprising coupling a fluid chamber to the nozzle by: disposing the nozzle within a cartridge defining the fluid chamber; and adhering an outer surface of the nozzle to an inner wall of the cartridge.

11. The method of claim 10, wherein adhering the outer surface of the nozzle to the inner wall of the cartridge comprises one of adhering the outer surface of the nozzle to the inner wall of the cartridge with an adhesive or adhering the outer surface of the nozzle to the inner wall of the cartridge by welding.

12. The method of claim 11, wherein adhering the outer surface of the nozzle to the inner wall of the cartridge comprises adhering the outer surface of the nozzle to the inner wall of the cartridge by laser welding.

13. The method of claim 10, wherein adhering the outer surface of the nozzle to the inner wall of the cartridge comprises adhering the outer surface of the nozzle to the inner wall of the cartridge in a position in which a lower periphery of the nozzle engages an internal shoulder portion of the cartridge.

14. The method of claim 10, wherein adhering the outer surface of the nozzle to the inner wall of the cartridge comprises adhering the outer surface of the nozzle to the inner wall of the cartridge in a position in which a lower periphery of the nozzle engages an outlet conduit of the cartridge on the opposite side of the nozzle from the fluid chamber.

15. The method of claim 1, wherein forming the nozzle comprises forming the nozzle from one of a polymer, a metal, or a glass.

16. The method of claim 15, wherein forming the nozzle comprises forming the nozzle from one or more of a cyclic olefin polymer, a cyclic olefin copolymer, polycarbonate, polypropylene, glass, or silicon borate.

17. The method of claim 1, further comprising locating the interior nozzle geometry within the nozzle and machining the sacrificial tip to a predetermined distance from the opening along the axis.

18. The method of claim 1, further comprising machining the sacrificial tip to remove material along the axis until the orifice reaches a predetermined size.

19. The method of claim 1, further comprising machining the sacrificial tip to remove material along the axis until a wall of the interior nozzle geometry at the orifice is parallel to the axis.

20. The method of claim 1, wherein the subtractive process includes machining a surface about the orifice normal to the axis of the nozzle.

21. The method of claim 1, wherein forming the nozzle includes injection molding the nozzle and sacrificial tip in a mold including:
    a first mold element that defines a hollow space; and
    a second mold element that fits in the hollow space defined in the first mold element and that includes a lower pin section that decreases in cross-sectional area until it terminates at a lower end that defines the orifice, the lower end displaced from an upper internal surface of a lower portion of the first mold element by a region defining the sacrificial tip when the second mold element is fully inserted into the first mold element.

* * * * *